United States Patent [19]

Mueller

[11] Patent Number: 4,948,643
[45] Date of Patent: Aug. 14, 1990

[54] FLEXIBLE MEDICAL SOLUTION TUBING

[75] Inventor: Walter B. Mueller, Inman, S.C.

[73] Assignee: W. R. Grace & Co.-Conn, Duncan, S.C.

[21] Appl. No.: 341,991

[22] Filed: Apr. 21, 1989

Related U.S. Application Data

[63] Continuation-in-part of Ser. No. 299,996, Jan. 23, 1989, abandoned.

[51] Int. Cl.$^5$ ............................................. F16L 11/04
[52] U.S. Cl. .................................. 428/36.6; 138/137; 428/36.7; 428/36.91; 428/423.1; 428/483; 428/516; 428/520
[58] Field of Search .................... 428/36.91, 35.7, 36.7, 428/36.6, 516, 423.1, 483, 520; 138/137, 140; 604/264, 280

[56] References Cited

U.S. PATENT DOCUMENTS

| | | | |
|---|---|---|---|
| 4,101,699 | 7/1978 | Stine et al. | 428/36.91 |
| 4,401,536 | 8/1983 | Lundell et al. | 204/159 |
| 4,436,778 | 3/1984 | Dugal | 428/36.7 |
| 4,551,140 | 11/1985 | Shinohara | 604/280 |
| 4,565,738 | 1/1986 | Purdy | 428/516 |
| 4,603,712 | 8/1986 | Krause | 428/516 |
| 4,627,844 | 12/1986 | Schmitt | 604/264 |
| 4,643,926 | 2/1987 | Mueller | 428/035 |

FOREIGN PATENT DOCUMENTS 0082665 4/1988 Japan.

*Primary Examiner*—James Seidleck
*Attorney, Agent, or Firm*—John J. Toney; William D. Lee, Jr.; Mark B. Quatt

[57] ABSTRACT

A medical solution tubing useful in combination with medical solution packages and pouches includes an intermediate layer comprising a polymeric material which imparts flexibility to the film; an inner layer comprising a heat resistant polymer; and an outer layer of polypropylene, ethylene propylene copolymer, or modified ethylene propylene copolymer.

5 Claims, 1 Drawing Sheet

FLEXIBLE MEDICAL SOLUTION TUBING

This application is a continuation-in-part of U.S. Ser. No. 299,996, filed Jan. 23, 1989 now abandoned.

This invention relates to autoclavable flexible tubing suitable for use with medical solution packaging.

Currently, it is common medical practice to supply liquids such as medical solutions for parenteral administration in the form of disposable, flexible pouches. These pouches should be characterized by collapsibility, transparency, and adequate mechanical strength. They must also be able to resist the relatively high temperatures required for heat sterilization of their contents, for example in an autoclave. Typically, medical solutions and the like are autoclaved at about 253° F. for periods of 15 to 30 minutes.

Connector tubing is used in combination with such flexible pouches. This tubing is used to introduce additional materials to the medical solution inside the pouch, and to administer the medical solution to the patient. This connector tubing must be chemically and physically compatible with the medical solution pouch material. The tubing must also be resistant to the heat generated during autoclaving of the medical solution pouch and tubing. When the tubing is used in combination with for example a polycarbonate connector, it sometimes must be sealable to the connector material by means of ultrasonic, radio frequency (RF) or heat sealing. In some cases, a pin heater is inserted into the tubing to heat the inside as well as the outside of the tubing. It is especially required of such tubing that it be flexible without embrittlement or cracking of the tubing. In this regard, it is known that polyvinyl chloride for example becomes brittle at relatively low temperatures.

Of particular interest is U.S. Pat. No. 4,643,926 issued to Mueller and assigned to a common assignee with the present application.

In the '926 patent, a flexible film suitable for medical solution pouches is disclosed. This film may include a sealant layer of ethylene propylene copolymer, modified ethylene propylene copolymer or flexible copolyester; at least one material layer of a polymeric material which imparts flexibility to the film, such as very low density polyethylene, ethylene propylene monomer blended with ethylene vinyl acetate copolymer, modified ethylene propylene copolymer, ethylene methyl acrylate copolymer, and modified ethylene vinyl acetate copolymer; and an outer layer of copolyester or ethylene propylene copolymer.

Of interest is U.S. Pat. No. 4,401,536 issued to Lundell et al which discloses the use of a blend of medical grade radiation-stabilized polypropylene and a copolymer of ethylene and a comonomer selected from the group consisting of vinyl esters of saturated carboxylic acids and alkyl esters of alpha, beta ethylenically unsaturated carboxylic acids, the blend being irradiated.

OBJECTS

It is an object of the present invention to provide a tubing suitable for use with medical solution packaging, the film tubing having good flexibility.

Another object of the present invention is to provide a tubing suitable for use with medical solution packaging characterized by compatibility with prior art packaging and ability to withstand autoclaving of the tubing.

DEFINITIONS

The term "flexible" is used herein to define specific polymeric materials as well as characteristics of a resulting tubing whereby improved flexibility and/or bendability is obtained by the use of these specific polymeric materials. Flexible materials may be characterized by a modulus of preferably less than 50,000 PSI (ASTM D-882-81) and more preferably less than 40,000 PSI (ASTM D-882-81).

The term "film" and the like refers to a thermoplastic material suitable for packaging and having one or more layers of polymeric materials which may be bonded by any suitable means well known in the art.

The term "polymer", "polymeric", and the like, unless specifically defined or otherwise limited, generally includes homopolymers, copolymers and terpolymers and blends and modifications thereof.

The term "intermediate" is used herein to refer to a layer of a multilayer film which is bonded on both of its major surfaces to another layer or film.

The term "melt flow" and "melt flow index" is used herein as the amount, in grams, of a thermoplastic resin which can be forced through a given orifice under a specified pressure and temperature within 10 minutes. The value should be determined in accordance with ASTM D 1238-79.

The term "very low density polyethylene" is used herein to define a copolymer of polyethylene with densities below 0.912 gm/cc, preferably between 0.900 to 0.906 gm/cc and including densities as low as 0.860 gm/cc, as measured by ASTM D-1505.

The term "ethylene vinyl acetate copolymer" (EVA) is used herein to refer to a copolymer formed from ethylene and vinyl acetate monomers wherein the ethylene derived units in the copolymer are present in major amounts and the vinyl acetate derived units in the copolymer are present in minor amounts.

The term "ethylene propylene copolymer" is used herein to refer to a copolymer formed from polypropylene monomer and minor amounts, usually less than 6%, of ethylene.

The term "copolyester" and the like is applied to polyesters synthesized from more than one diol and a dibasic acid. Copolyesters as used herein may also be characterized as copolymers of polyether and polyethylene terephthalate. More preferably copolyesters as used herein may be characterized as polymeric materials derived from 1,4 cyclohexane dimethanol, 1,4 cyclohexane dicarboxylic acid, and polytetramethylene glycol ether, or equivalents of any of the above, as reactants.

The term "modified" and the like is used herein to refer to a polymeric material in which some or all of the substituents are replaced by other materials, providing a change in properties such as improved flexibility or elastomeric properties. For example, a modified ethylene propylene copolymer is for example an ethylene propylene copolymer to which an elastomeric material such as Kraton rubber has been added by any means.

SUMMARY OF THE INVENTION

A polymeric tubing useful for medical applications comprises an intermediate layer comprising a polymeric material which imparts flexibility to the film; an inner layer, bonded to an inner surface of the intermediate layer, and comprising a polymeric material which is heat resistant; and an outer layer, bonded to an outer surface of the intermediate layer, and comprising a polymeric material selected from the group consisting of polypropylene, ethylene propylene copolymer, and modified ethylene propylene copolymer.

DETAILED DESCRIPTION OF THE PREFERRED EMBODIMENTS

Figure 1:
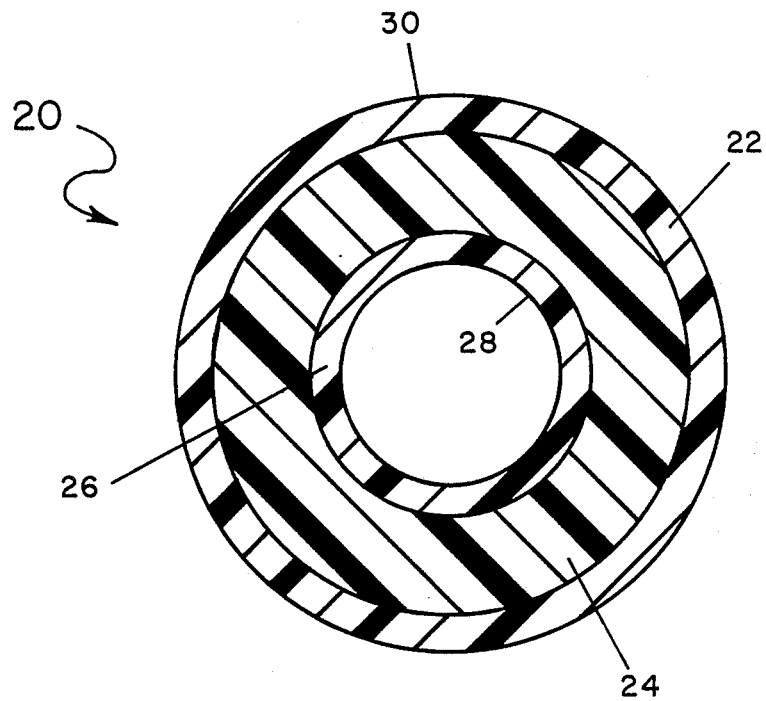
FIG. 1 is a schematic cross-section of a three layer tubing made in accordance with the invention.

FIG. 1 shows a three layer tubing 20 in accordance with the invention. Outer layer 22 is an ethylene propylene copolymer (EPC) or modified EPC. A suitable EPC is Eltex KS 409X6206 available from Solvay. This copolymer has an ethylene content of about 3.8%. A suitable modified EPC is Cosden Z4650 available from Cosden Chemical Company and containing a blend of ethylene propylene copolymer and styrene ethylene butylene styrene copolymer. Polyallomers may also be used, such as ethylene propylene block copolymer, available from Eastman as M7853-368A, having a melt flow index of about 12. The outer layer 22 will be in contact at one end with a connector such as a polycarbonate connector. Outer layer 22 will sometimes require sealability with the polycarbonate or other connector material. Sealing may be by ultrasonic sealing, heat sealing, or RF sealing depending on the materials used.

Intermediate layer 24 may be any of various materials which impart flexibility to the resulting film. Especially preferred materials include very low density polyethylene (VLDPE) such as DEFD 1362, ethylene methyl acrylate copolymer (EMA) such as commercially available Gulf resin 2205 having 20% methyl acrylate and a density of 0.942 and a melt index of about 2.4; and ethylene vinyl acetate copolymer (EVA) such as du Pont Alathon 3175 having a vinyl acetate content of about 28% by weight of the copolymer.

Modified ethylene methyl acrylate copolymer such as Plexar 3382 is also useful for intermediate layer 24.

Blends such as EVA and modified EMA, and VLDPE and modified EMA, may also be used in intermediate layer 24. These blends offer the flexibility provided by EVA or VLDPE, and the adhesive qualities provided by the modified EMA. Other suitable adhesives can be substituted for the modified EMA.

A blend of EVA and VLDPE may also be used, but will have less desirable adhesive properties than the other blends mentioned above.

Blends of more than two of these blend components can also be used in layer 24.

Where radiation frequency (RF) sealability is desired, polyvinyl chloride or polyvinylidene chloride materials may be used for the intermediate layer.

Modified ethylene vinyl acetate copolymer may also be used in intermediate layer 24.

Inner layer 26 of the three layer embodiment of the present invention is preferably ethylene propylene copolymer, or a flexible copolyester, more preferably a copolymer of polyether and polyethylene terephthalate, such as Eastman PCCE 9967 from Eastman Chemical Products, Inc. Other suitable flexible copolyesters are PCCE 9964, PCCE 9965, and PCCE 9966, available from Eastman. These particular copolyesters are characterized by inherent viscosities ranging from 1.05 to 1.28, and by the use of 1,4 cyclohexane dimethanol, 1,4 cyclohexane dicarboxylic acid, and polytetramethylene glycol ether as reactants in producing the flexible copolyester. Polypropylene may also be used in inner layer 26. The materials of inner layer 26 are especially chosen for their heat resistance so that the tubing may be autoclaved along with the accompanying medical solution pouch and still maintain its structural integrity. Polyurethane, PVC, or a blend of copolyester and EVA may also be used in inner layer 26.

The tubing after coextrusion by conventional means may optionally be cross-linked by radiation techniques well known in the art. This irradiation may strengthen the tubing particularly for autoclaving purposes. Alternatively, a chemical cross-linking agent may be introduced to the resin melt of any or all of the layer discussed above prior to extrusion to effect the cross-linking of the tubing.

EXAMPLES

Exemplary multi-layer structures are coextruded and irradiated. These structures are viewed as potential replacements for polyvinyl chloride tubing. Examples 1 through 5, in part reflected in the detailed description of the preferred embodiments hereinbefore described, are listed below with their respective formulations, beginning with the outer layer and ending with the inner layer. Unless otherwise denoted, Examples 1-5 included the following materials:
EPC: Eltex KS409x6206;
Modified EMA: Plexar 3382;
Modified EPC: Z4650;
flexible copolyester: PCCE 9967;
EVA: ELVAX 3175; and
VLDPE: DEFD 1362;

In Example 1 the multilayer film comprised modified EPC/VLDPE/flexible copolyester.

In Example 2, the multi-layer film comprised modified EPC/EVA/flexible copolyester.

In Example 3, the multi-layer film comprised EPC/modified EMA/flexible copolyester.

In Example 4, the multi-layer film comprised EPC/Plexar 3382/EPC.

In Example 5, the multi-layer film comprised EPC/EVA/EPC.

The films of Examples 4 and 5 are stiffer and less flexible than the films of Examples 1 to 3.

It should be noted that the detailed description and specific examples which indicate the presently preferred embodiments of the invention are given by way of illustration only. Various changes and modifications within the spirit and scope of the claims will become apparent to those of ordinary skill in the art upon review of the above detailed description and examples.

What is claimed is:
1. A polymeric tubing useful for medical applications comprising:
   (a) an intermediate layer comprising a polymeric material selected from the group consisting of very low density polyethylene, ethylene vinyl acetate copolymer, ethylene methyl acrylate copolymer, modified ethylene methyl acrylate copolymer, polyvinyl chloride, a blend of ethylene vinyl acetate copolymer and modified ethylene methyl acrylate copolymer, a blend of very low density polyethylene and modified ethylene methyl acrylate copolymer, a blend of ethylene vinyl acetate copolymer and very low density polyethylene, and modified ethylene vinyl acetate copolymer;

(b) an inner layer, bonded to an inner surface of the intermediate layer, and comprising a polymeric material selected from the group consisting of copolyester, polypropylene, ethylene propylene copolymer, polyurethane, polyvinyl chloride, and a blend of copolyester and ethylene vinyl acetate copolymer; and (c) an outer layer, bonded to an outer surface of the intermediate layer, and comprising a polymeric material selected from the group consisting of polypropylene, ethylene propylene copolymer, and modified ethylene propylene copolymer.

2. The tubing of claim 1 wherein the ethylene vinyl acetate copolymer of the intermediate layer has a vinyl acetate content by weight of the copolymer of between about 15% and 30%.

3. The tubing of claim 1 wherein the modified ethylene methyl acrylate copolymer of the intermediate layer includes carboxylic acid or acid anhydride moieties.

4. The polymeric tubing of claim 1 wherein the tubing is cross-linked.

5. The polymeric tubing of claim 4 wherein the tubing is cross-linked by irradiation.

* * * * *